United States Patent [19]

Mayer

[11] Patent Number: 4,487,723
[45] Date of Patent: Dec. 11, 1984

[54] SUBSTITUTED-BUTANEDIPEROXOIC ACIDS AND PROCESS FOR BLEACHING

[75] Inventor: James M. Mayer, Maryland Heights, Mo.

[73] Assignee: Monsanto Company, St. Louis, Mo.

[21] Appl. No.: 336,542

[22] Filed: Jan. 4, 1982

[51] Int. Cl.³ ............................................. C07C 179/10
[52] U.S. Cl. ............................. 260/502 R; 252/186.42
[58] Field of Search ........................ 260/502 R, 453 R, 186.22–186.24; 252/186.21

[56] References Cited

U.S. PATENT DOCUMENTS

| | | | |
|---|---|---|---|
| 2,377,038 | 5/1945 | Reichert et al. | 260/502 R |
| 2,813,896 | 11/1957 | Krimm | 260/502 |
| 3,959,163 | 5/1976 | Farley | 252/99 |
| 4,013,581 | 3/1977 | Huber | 252/186 |
| 4,094,808 | 6/1978 | Stewart et al. | 252/186 |
| 4,126,573 | 11/1978 | Johnston | 252/99 |
| 4,134,850 | 1/1979 | McCrudden | 252/186 |
| 4,233,235 | 11/1980 | Camden et al. | 260/502 R |
| 4,391,723 | 7/1983 | Bacon et al. | 252/90 |
| 4,391,724 | 7/1983 | Bacon | 252/90 |
| 4,391,725 | 7/1983 | Bossu | 252/186 |

FOREIGN PATENT DOCUMENTS 18527  8/1968  Japan ................................. 568/566

*Primary Examiner*—Werren B. Lone
*Attorney, Agent, or Firm*—R. C. Griesbauer; J. C. Logomasini; A. H. Cole

[57] ABSTRACT

Substituted-butanediperoxoic acids represented by the formula

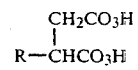

wherein R is alkyl of 6 to 18 carbon atoms or phenyl are useful oxidizing agents. These substituted-butanediperoxoic acids are useful as bleaching agents and disinfecting agents.

6 Claims, No Drawings

SUBSTITUTED-BUTANEDIPEROXOIC ACIDS AND PROCESS FOR BLEACHING

This invention relates to substituted-butane-diperoxoic acids which are useful as bleaching agents and disinfecting agents.

BACKGROUND OF THE INVENTION

The property possessed by some materials of bleaching articles is known and widely used to remove discoloration or stains from articles. The behavior and mechanisms by which such bleaching agents perform their functions are only partially understood. It is known that many colored materials contain a conjugated chain, that is, a series of double bonds which alternate with single bonds. If one of the double bonds is broken the color is usually destroyed, therefore, an agent which will remove a double-bond linkage may be an effective bleach. A bleaching agent may also act on the groups at the ends of the chain. Bleaching materials are generally categorized as chlorine; hypochlorites and chloramines; hydrogen peroxide and other peroxy compounds; chlorite and chlorine dioxide; and reducing agents.

The need for bleaching agents is growing in view of energy conservation and environmental protection measures. For example, in the detergent industry improved cleansing of fabrics is being sought since washing performance has suffered because of lower wash temperatures, reduced use of phosphate builders and increased use of synthetic fabrics. The use of new bleaching agents is an effective way to restore this lost performance.

A number of peroxy compounds have been evaluated as bleaching agents and some of these have been diperoxoic acids. For example, U.S. Pat. Nos. 3,959,163 and 4,094,808 disclose bleach compositions where the active agent is diperisophthalic acid; U.S. Pat. No. 4,134,850 discloses bleaching compositions where the active agent is a cycloaliphaticdiperoxoic acid; and U.S. Pat. Nos. 2,813,896 and 4,126,573 disclose bleaching compositions where the active agent is an alpha omega long chain aliphatic diperoxoic acid.

Although satisfactory results are achieved using the diperoxoic acids set forth above, there remains a need for new and structurally different diperoxoic acids to satisfy specialized applications in home laundry bleaching. Hence, those skilled in the art of bleach formulation are constantly looking for peroxy compounds for use as bleaching agents in such formulations, and the present invention provides to the art a class of diperoxoic acids that are structurally different from the prior art suitable for use in such applications.

SUMMARY OF THE INVENTION

These advantages are achieved by a compound represented by the formula:

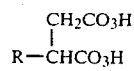

wherein R is alkyl of 6 to 18 carbon atoms or phenyl.

Also, in accordance with the present invention there is provided a process for bleaching articles which comprises contacting articles to be bleached with an aqueous medium containing a bleach effective amount of a compound represented by the formula:

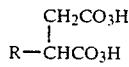

wherein R is alkyl of 6 to 18 carbon atoms or phenyl, and mixtures thereof.

For home laundry bleaching, for example, the process for bleaching can be conducted as a fabric presoak or with the washing process.

Broadly described, the compounds of the instant invention can be prepared by bringing together under reaction conditions a substituted-succinic acid or anhydride with hydrogen peroxide.

Where R in the above formula is phenyl, it can be substituted phenyl group having noninterfering substituents, such as, chlorophenyl, nitrophenyl, lower-alkylphenyl and the like.

Where R is alkyl, straight chain alkyl groups are preferred. Particularly preferred are alkyl of 8 to 14 carbon atoms.

The substituted-butanediperoxoic acids of this invention are solids at room temperature and are water-soluble or water-dispersible which in aqueous medium provides a —O—O—moiety.

The substituted-butanediperoxoic acids of the present invention tend to lose their active oxygen when subjected to elevated temperatures, the presence of heavy metals, excessive pH and the like.

The substituted-butanediperoxoic acids are conveniently employed as the primary bleaching agent in the form of particulate solids in granular or powder formulations containing diluents and stabilizers to retard the loss of its active oxygen. The amount of active oxygen is determined by multiplying the two peroxoic groups in the compound by 16, the atomic weight of oxygen, and dividing the product by the molecular weight of the compound.

Suitable stabilizers to prevent exothermic decomposition of these compounds are those which are capable of liberating moisture at a temperature below the decomposition of the particular substituted-butane-diperoxoic acid compound. A wide variety of suitable exotherm control materials can be used and include hydrated materials, such as potassium aluminum sulfate dodecahydrate, magnesium sulfate heptahydrate, sodium aluminum sulfate dodecahydrate, magnesium ammonium sulfate hexhydrate, acids, such as boric acid, malic acid, maleic acid, succinic acid, substituted-succinic acids, azelaic acid, dodecanedioic acid, cyclohexane dicarboxylic acid and the like. Boric acid is preferred.

Suitable stabilizers to prevent catalytic decomposition of the instant compounds in the presence of heavy metals, for example, iron and copper, are chelating agents. Suitable chelating agents are alkali metal polyphosphates, 8-hydroxyquinoline, ethylenediamine tetra acetic acid, 1-hydroxy-ethylidene diphosphonic acid, aminotri (methylene phosphonic acid), phosphoric acid and mixtures thereof. Phosphoric acid or a mixture of phosphoric acid and tetrasodium pyrophosphate is preferred.

In addition to the chelating agents and exotherm control agents mentioned above, coating materials can also be used to extend the shelf life of dry formulations containing the substituted-butanediperoxoic acid compounds of this invention as the primary bleaching agent. Suitable coating materials include a wide variety of fatty acids, fatty alcohols, derivatives thereof, such as esters and ethers, derivatives of polyethylene glycols, such as esters and ethers, hydrocarbon oils and waxes. These materials not only aid in preventing moisture from reaching the compound but can also be used to segregate the compound from other agents which may be present in the formulation and adversely affect the compound's stability.

A diluent is optionally employed as a processing aid in the formulation to adjust the concentration of the compounds of the instant invention as the primary bleaching agent and to facilitate handling, shipping and subsequent addition to the wash water or blending with additional detergent materials such as surfactants, builders, anti-static agents, coloring agents, bleach activators, perfumes and the like prior to addition to wash water. The diluent or processing aid can conveniently be used in an amount to provide a formulation containing from about 30 to 60 percent by weight of the active substituted-butanediperoxoic acid, from about 1 to 5 percent by weight chelating agent, from about 15 to 55 percent by weight exotherm control agent. A preferred diluent is sodium sulfate which is compatible with the stabilizers as well as ingredients in detergent formulations.

Generally, the process for bleaching in accordance with present invention is conducted to provide at least 1 ppm avilable oxygen from the substituted-butanediperoxoic acid in the solution contacting the articles to be bleached. For bleaching textile fabrics, for example, cotton or cotton/polyester about 5 to 100 ppm active oxygen are used. Where the article is other than textile fabrics, such as, wood, plastic or metal surfaces about 75 to 300 ppm or more are used. Where desired the process of the instant invention can be used to bleach fibers, textiles, wood, paper or pulp using conditions and equipment employed with hydrogen peroxide or inorganic peroxides.

In conducting the bleaching process in home laundry the present bleaching process can take place at ambient temperature or higher, conveniently in the range of 25° to 60° C. It is particularly convenient to conduct the present bleaching process simultaneously with the washing process by contacting the textile fabrics with a water solution or dispersion of the substituted-butanediperoxoic acid compound and a laundry detergent.

DETAILED DESCRIPTION OF THE INVENTION

The invention is further illustrated and demonstrated by, but not limited to, the following examples wherein all parts are by weight unless otherwise indicated.

EXAMPLE I

Octylbutanediperoxoic Acid

To 2.8 grams of n-octylsuccinic anhydride in an open beaker fitted with a magnetic stirrer was added 20 ml of methanesulfonic acid and the mixture was heated to about 60° C. to dissolve the anhydride. The solution was cooled to about 50° C. and 1.5 ml of 90% hydrogen peroxide was added at an initial rate of 0.05 ml/min. The rate of addition was increased to 0.25 ml/min toward the end of the addition. The solution was maintained at 40°-50° C. for one hour and was then allowed to cool to ambient. After a total of four hours the reaction mixture was cooled to 10° C. and quenched by pouring over ice. The solid product was filtered and was rinsed with 5×10 ml of ice water. The product was allowed to air dry in a glass dish. The product weighed 2.35 grams and a standard potassium iodide-thiosulfate titration showed 11.27% (12.20% theory)active oxygen. An IR spectrum of the product, n-octyl-butanediperoxoic acid, exhibited the peroxoic bands at 3.10 and 5.75 microns.

EXAMPLE II

Dodecylbutanediperoxoic Acid

To 2.7 grams of n-dodecylsuccinic anhydride in an open beaker fitted with a magnetic stirrer was added 20 ml of methanesulfonic acid. The mixture was heated to 65° C. and stirred to dissolve all the anhydride. The solution was cooled to 45° C. and the addition of 1.5 ml of 90% hydrogen peroxide at a rate of 0.10 ml/min. was begun using stirring and gentle external heating to maintain the temperature at 45° C. After 1 ml of the hydrogen peroxide had been added an additional 5.0 ml of methanesulfonic acid was added to reestablish stirring and the remaining hydrogen peroxide was added with stirring at 40°-50° C. After a total of four hours the reaction mixture was cooled to 10° C. and quenched by pouring over ice. The solid product was filtered and rinsed with 5×10 ml of ice water and allowed to air dry. The product, n-dodecylbutanediperoxoic acid, weighed 2.5 grams and contained 9.50% (10.05% theory) active oxygen.

EXAMPLE III

Phenylbutanediperoxoic Acid

To 2.5 grams of phenylsuccinic acid in an open beaker fitted with a magnetic stirrer was added 10.0 ml of methanesulfonic acid. With stirring 5.0 ml of 50% hydrogen peroxide was added slowly, a solid precipitated and the reaction mixture was heated to 55° C. for about 1.5 hours with stirring and then allowed to cool to ambient. After about a total of four hours the reaction mixture was cooled to about 10° C. and poured into 50 ml of 5° C. saturated ammonium sulfate solution. The precipitate was filtered and rinsed three times with cold saturated ammonium sulfate solution. The product was let dry on the filter for about 1 hour and then scraped into a culture dish and allowed to dry in the hood to yield phenylbutanediperoxoic acid of 11.49% (14.16% theory) active oxygen.

EXAMPLE IV

Octadecylbutanediperoxoic Acid

To 2.5 grams of octadecylsuccinic anhydride in an open beaker fitted with a magnetic stirrer was added 20 ml of methanesulfonic acid and the mixture was heated to 90° C. to effect solution. The mixture solidified upon cooling with ice to about 60° C. which was broken up and 10 ml of methanesulfonic acid was added to provide a stirrable mixture. The mixture was cooled to 25° C. and 5.0 ml of 50% hydrogen peroxide was added at a rate of 0.20 ml/min while continuing to cool with ice. Upon completion of the addition of the hydrogen peroxide the temperature was 15° C. and the reaction mixture was allowed to warm to ambient temperature. About 3 hours after completion of the addition of hydrogen peroxide a test sample, 0.75 ml, was added to 1 ml of ice water and extracted with 3 ml of ethylether and dried over sodium sulfate. Titration of the product showed 2.84% active oxygen. The reaction mixture was heated to about 45° C. for about 2 hours then cooled to 20° C. and quenched by mixing with 75 ml of ice water. The slurry was filtered, extracted with ethylether and dried to provide n-octadecylbutanediperoxoic acid of 6.72% (7.95% theory) active oxygen.

EXAMPLE V

Decylbutanediperoxoic Acid

Following the general procedure of Example IV using n-decylsuccinic anhydride in place of the n-octadecylsuccinic anhydride yielded n-decylbutanediperoxoic acid of 10.40% (11.02% theory) active oxygen.

The bleaching properties of representative substituted-butanediperoxoic acids of the present invention were evaluated and compared to known alpha, omega dodecanediperoxoic acid, see for example, U.S. Pat. Nos. 2,813,896 and 4,259,201. For comparative purposes, each diperoxoic acid was titrated to determine the active oxygen content and its comparative performance was based upon active oxygen levels. For example, tests were run to compare the bleaching rates on stains in solution. The tests were run by preparing aqueous dispersion of the substituted-butanediperoxoic acid at several levels, 40, 20, 10, 5, 2 and 1 parts per million (ppm) active oxygen and comparing it to alpha, omega dodecanediperoxoic acid at the intermediate level of 20 ppm active oxygen. The tests were conducted by adding a concentrated detergent solution, $C_{11}$ linear alkylbenzene sodium sulfonate and pentasodium tripolyphosphate, that contained the test stain. The level of active oxygen in ppm from octylbutanediperoxoic acid (Compound A) from octadecylbutanediperoxoic acid (Compound B) and from dodecylbutanediperoxoic acid (Compound C) which gave equivalent performance to the alpha, omega dodecanediperoxoic acid (Compound D) at the use level of 20 ppm active oxygen was noted. The results are shown in Table I.

TABLE I

| Stain or Dye | Active oxygen level in ppm to obtain equivalent performance from: | | | |
|---|---|---|---|---|
| | Compound A | Compound B | Compound C | Compound D |
| Brilliant Blue G | 1 | 7 | 1.5 | 20 |
| Alizarin Red | 15 | >40 | >40 | 20 |
| Chlorophyll | 4 | 20 | 4 | 20 |
| Methyl orange | 6 | — | 15 | 20 |

The chlorophyll stain was a methanol extract of spinach that also contained some carotenes. The carotenes were bleached more slowly than was the chlorophyll. The relative bleaching rates in solution vary. Chlorophyll and the blue dye bleached much faster than the red or orange dyes.

Tests were run to substantiate that the differences in performance are reflected in bleaching stains from fabrics. Both cotton and polyester/cotton test swatches were stained by spotting with concentrated solutions of chlorophyll, Brilliant Blue G and grape juice. The stains were set by first drying at room temperature and then in a dryer at medium heat. The swatches were washed in Terg-o-Tometer in 500 ml of wash solution. The solution contained 0.75 grams of Tide detergent and 75 mg. (ca. 15 ppm of active oxygen) of octylbutanediperoxoic acid or alpha, omega dodecanediperoxoic acid. Perborate (80 mg) was also tested for comparison. The swatches were washed for 10 minutes and were then rinsed well and dried. Little improvement was observed when perborate was used. Both diperoxoic acids were visibly better than perborate. Octylbutanediperoxoic acid was better than alpha, omega dodecanediperoxoic acid on chlorophyll and Brilliant Blue G and equal on grape juice.

Although the invention has been described in terms of specific embodiments which are set forth in considerable detail, it should be understood that this is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

What is claimed is:

1. A compound represented by the formula:

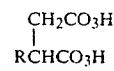

wherein R is alkyl of 10 to 18 carbon atoms or phenyl.

2. The compound of claim 1 wherein R is alkyl.

3. The compound of claim 1 wherein R is phenyl.

4. The compound of claim 2 represented by the formula:

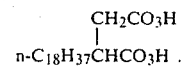

5. The compound of claim 2 represented by the formula:

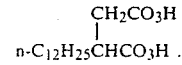

6. The compound of claim 2 represented by the formula:

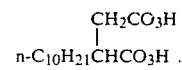

* * * * *